(12) United States Patent
Burdea et al.

(10) Patent No.: US 8,758,020 B2
(45) Date of Patent: Jun. 24, 2014

(54) PERIODIC EVALUATION AND TELEREHABILITATION SYSTEMS AND METHODS

(76) Inventors: Grigore Burdea, Highland Park, NJ (US); Moustafa Abdelbaky, North Brunswick, NJ (US); Bryan Rabin, North Brunswick, NJ (US)

( * ) Notice: Subject to any disclaimer, the term of this patent is extended or adjusted under 35 U.S.C. 154(b) by 1338 days.

(21) Appl. No.: 12/117,991

(22) Filed: May 9, 2008

(65) Prior Publication Data
US 2008/0281633 A1 Nov. 13, 2008

Related U.S. Application Data

(60) Provisional application No. 60/928,593, filed on May 10, 2007.

(51) Int. Cl.
*A63B 69/00* (2006.01)

(52) U.S. Cl.
USPC .................................. 434/247; 482/9; 705/2

(58) Field of Classification Search
CPC .............. G09B 19/003; G06F 19/3418; A63B 24/0003; A63F 2300/8082
USPC ................. 434/247, 255, 258; 482/1, 9; 705/2
See application file for complete search history.

(56) References Cited

U.S. PATENT DOCUMENTS

| | | | |
|---|---|---|---|
| 5,940,801 | A | 8/1999 | Brown |
| 6,613,000 | B1 | 9/2003 | Reinkensmeyer et al. |
| 6,749,432 | B2 * | 6/2004 | French et al. .................. 434/247 |
| 2003/0017438 | A1 * | 1/2003 | Ebersole et al. .............. 434/226 |
| 2003/0125099 | A1 | 7/2003 | Basson et al. |
| 2003/0149344 | A1 | 8/2003 | Nizan |
| 2003/0171190 | A1 * | 9/2003 | Rice ................................ 482/57 |
| 2006/0057549 | A1 * | 3/2006 | Prinzel et al. ................. 434/247 |
| 2006/0277074 | A1 | 12/2006 | Einav et al. |
| 2007/0033068 | A1 * | 2/2007 | Rao et al. .......................... 705/2 |
| 2007/0035831 | A1 | 2/2007 | Gutierrez Novelo |
| 2007/0050212 | A1 * | 3/2007 | Kearby et al. ..................... 705/3 |
| 2007/0087901 | A1 * | 4/2007 | Brassil et al. ................... 482/44 |

FOREIGN PATENT DOCUMENTS

WO    WO-2006/088415    8/2006

OTHER PUBLICATIONS

Extended EP Search Report in S/N 08 75 4325, dated Jan. 13, 2012, 7 pgs.
PCT International Search Report in PCT/US08/05995, mailed Jul. 16, 2008, 3 pgs.

* cited by examiner

*Primary Examiner* — Peter Egloff

(57) ABSTRACT

The present invention relates to a system and method for periodic evaluation and telerehabilitation in which a portable device is adapted to be held or coupled to a body part. For example, the portable device can be a cell phone. The body part can be, for example, the hand, ankle, torso, forearm or upper arm. An animated or virtual reality sequence forming a videogame runs or the portable device. Upon interaction of the user with the videogame, movement of the body part is captured as exercise data. The exercise data can be forwarded and stored at a remote clinical server. The system provides monitoring and scheduling of a therapy session by a clinician/doctor/therapist to control the exercises, length and/or difficulty of the exercises based on recorded data. In one embodiment, vital signs or body temperature are monitored by sensors on the portable device or by vital sign monitors associated with the user. The vital sign data can be synchronized with the exercise data at the remote clinical server, and used to improve patient safety during home therapy sessions.

27 Claims, 10 Drawing Sheets

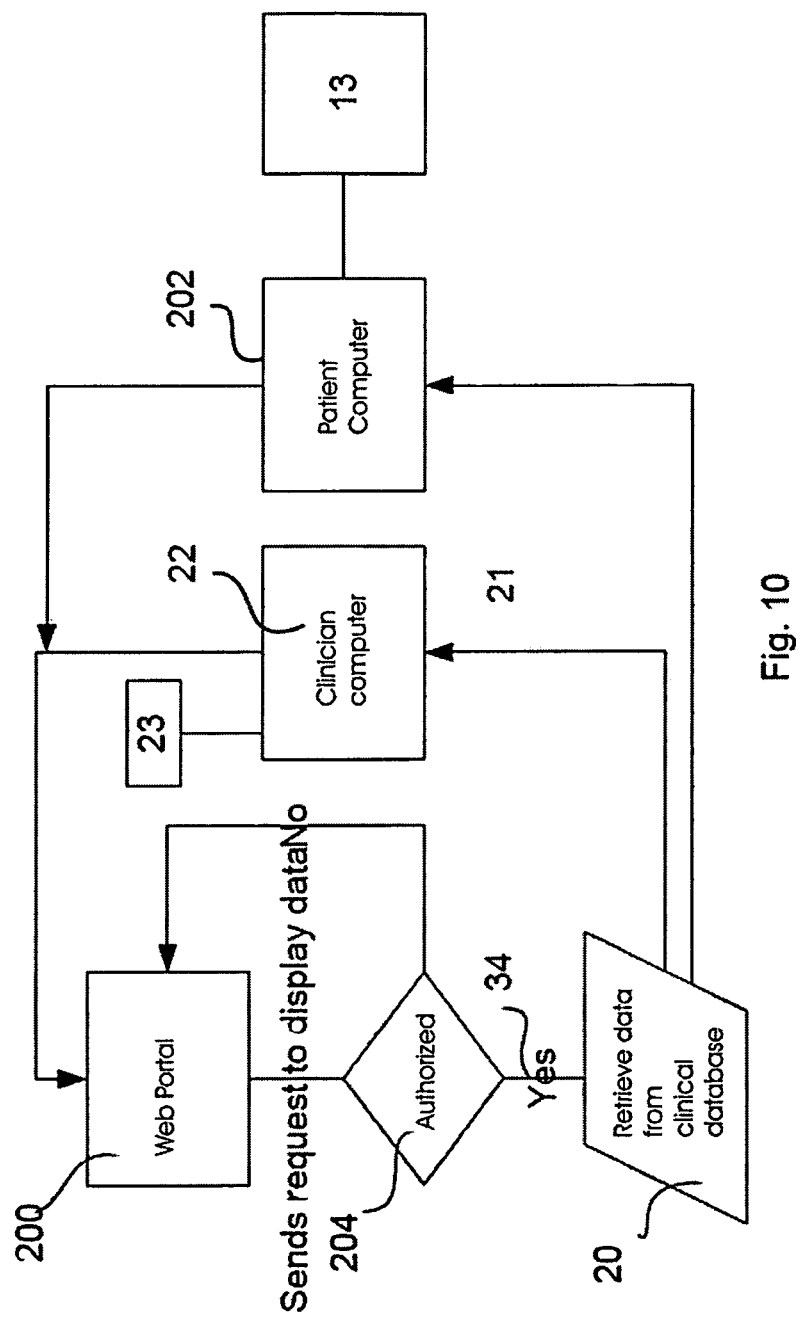

PERIODIC EVALUATION AND TELEREHABILITATION SYSTEMS AND METHODS

CROSS REFERENCE TO RELATED APPLICATION

This application claims the benefit of U.S. Provisional Patent Application No. 60/928,593 filed May 10, 2007 the entirety of each of which is hereby incorporated by reference into this application.

BACKGROUND OF THE INVENTION

1. Field of the Invention

The invention is a system and method for providing periodic evaluation and rehabilitation to patients in their home or while on travel. The invention integrates videogames with additional software layers to transform a hand-held communication device (such as a cell phone or BlackBerry®) into a rehabilitation device. Finally, the system allows monitoring and coaching of the patient by a remote clinician as well as online storage of data obtained by the hand held communication device (for example, a cell phone) during periodic evaluation and rehabilitation.

2. Description of Related Art

Several patents describe networked systems for remote health monitoring. U.S. Pat. No. 5,997,476 describes a networked system for communicating information to an individual and remotely monitoring the individual. The system includes a remote interface of a personal computer and a server. The apparatus interacts with the individual in accordance with a script received from the server. The script is programmed to communicate queries to the individual, receive responses to the queries and transmit the responses to the server.

A Wearable Wireless Body Area Network of Intelligent motion sensors has been described Jovanov et al. "A Wireless Body Area Network of Intelligent Motion Sensors for Computer Assisted Physical Rehabilitation", Journal of NeuroEngineering and Rehabilitation, 2:6 (2005). The system includes sensors that communicate wirelessly with a personal server. The sensors include accelerators and gyroscopes attached to body parts of the user. The personal server communicates with a remote health care server and servers of related services. The personal server provides an audio and graphical user interface to relay early warnings or guidance to the user.

U.S. Pat. No. 5,940,801 describes a diagnostic assessment of physiological conditions which employs a videogame. Information from the videogame such as a sequence of tasks and reaction time can be analyzed to determine whether clinical therapy and/or medication may be required.

It is desirable to provide a telerehabilitation system for remote periodic evaluation and rehabilitation of a patient in which a portable device including a multitude of videogames can be used to receive finger, wrist and/or arm movements, and/or another movement of other various appendages during play for exercising and the movements of the fingers, wrists, arms and/or other appendages are remotely monitored such that exercise can be scheduled and monitored based on the received data.

SUMMARY OF THE INVENTION

The present invention relates to a system and method for periodic evaluation and telerehabilitation in which a portable device is adapted to be held or coupled to a body part. For example, the portable device can be a cell phone. The body part can be, for example, the hand, ankle, torso, forearm or upper arm. An animated or virtual reality sequence forming a videogame runs or the portable device. Upon interaction of the user with the videogame, movement of the body part is captured as exercise data. The exercise data can be forwarded and stored at a remote clinical server. The system provides monitoring and scheduling of a therapy session by a clinician/doctor/therapist to control the exercises, length and/or difficulty of the exercises based on recorded data.

In one embodiment, vital signs or body temperature are monitored by sensors on the portable device or by vital sign monitors associated with the user. The vital sign data can be synchronized with the exercise data at the remote clinical server. The therapy session can be interrupted if the vital sign data exceeds a threshold and the remote clinician/doctor/therapist can be notified. The system can include a display such as a stereoscopic 3D television for displaying the videogame.

The invention will be more fully described by reference to the following drawings.

BRIEF DESCRIPTION OF THE DRAWINGS

FIG. 10 is a flow diagram of a web portal used for data retrieval and secure visualization in the periodic evaluation and telerehabilitation system.

DETAILED DESCRIPTION

Figure 1:
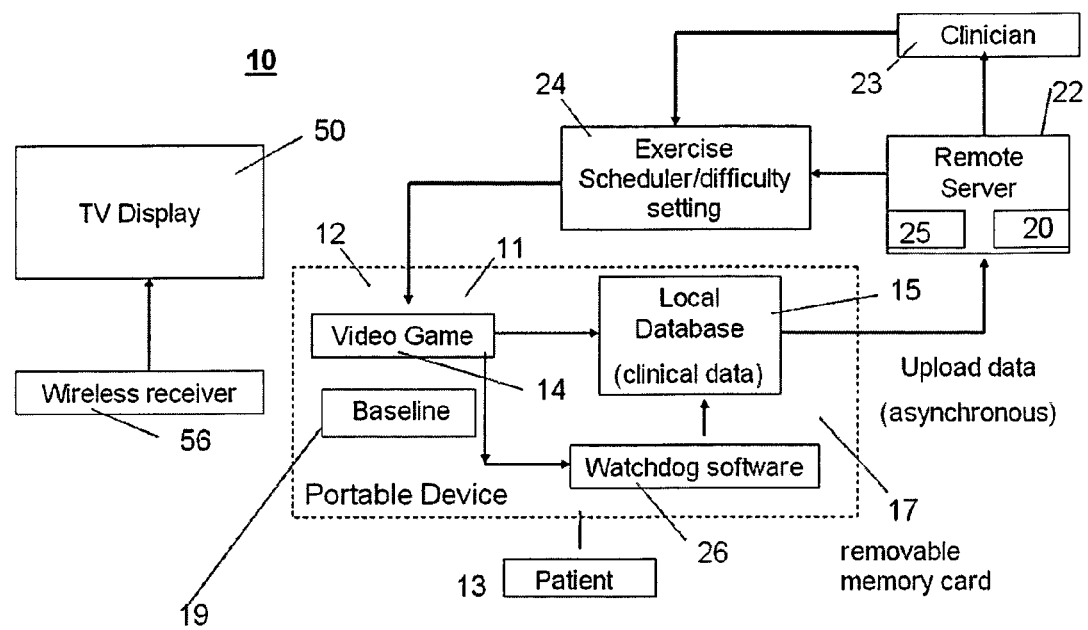
FIG. 1 is a schematic diagram of periodic evaluation and telerehabilitation system for a single user in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
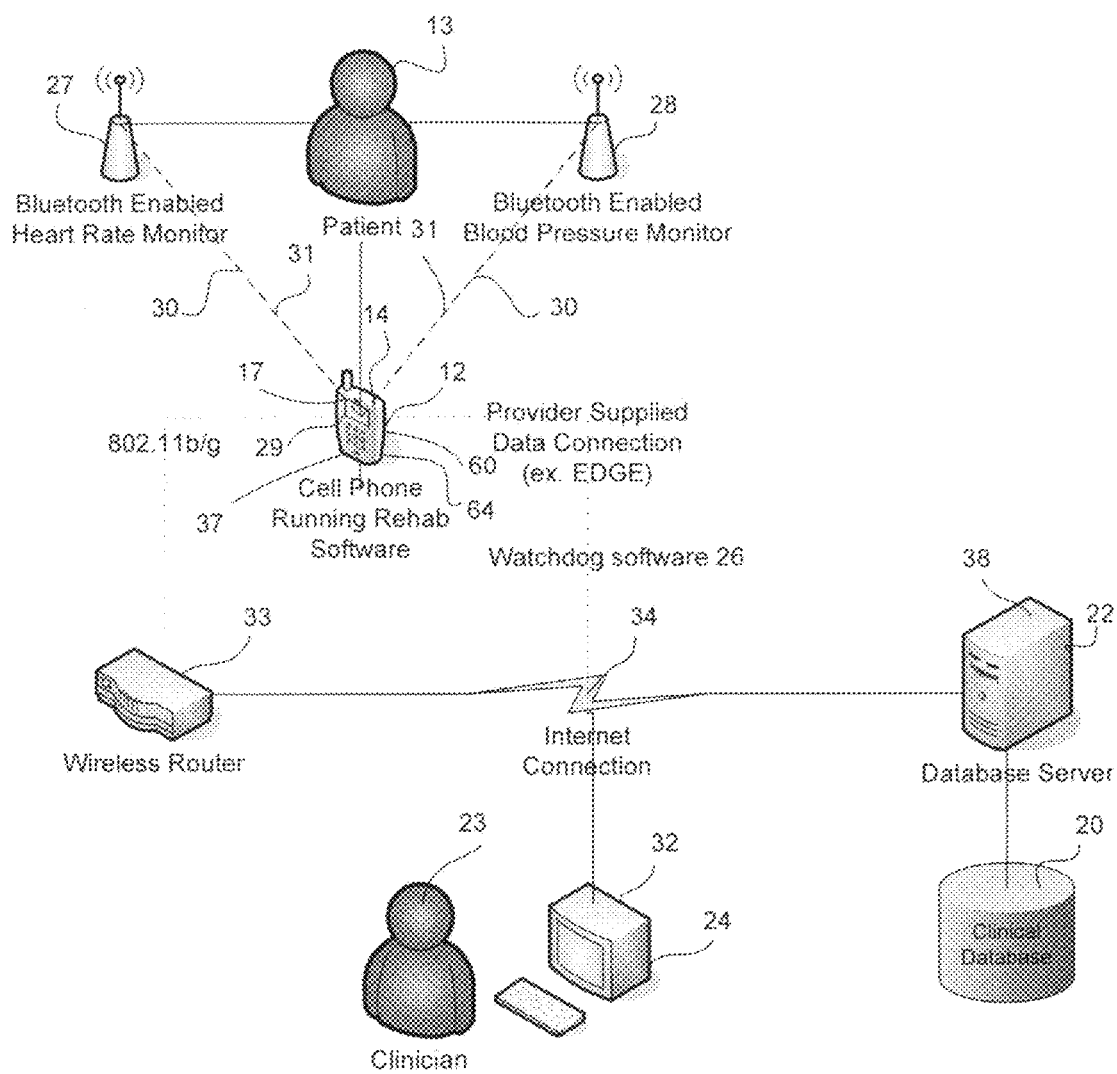
FIG. 2 is a schematic diagram of the periodic evaluation and telerehabilitation system integrated with vital sign monitoring devices.

Periodic evaluation and telerehabilitation system 10 for a single user in accordance with the teachings of the present invention is shown in FIG. 1. Screen 11 can be associated with portable device 12. Portable device 12 can be held in the hand of patient 13. For example, portable device 12 can be a cell phone. In the following invention description the term cell phone is understood to include cell phone, BlackBerry®, PDAs, iPhones and similar hand-held communication devices with on-board processing, sensing, communication and memory storage capabilities. Videogame 14 runs in portable device 12. In this embodiment it is envisioned that a multitude of videogames can be used, based on user's needs. The term videogame is thus understood to mean one, or several such games. Videogame 14 elicits, for example, finger, wrist and arm movements of patient 13 in order to play it. Videogame 14 can be an animated or virtual reality sequence. Various videogames can be switched in to portable device 12 in order to allow sufficient rehabilitation time without burden, and the type of games can be selected to be appropriate for the condition/disability for a particular patient 13. For example, videogames can be of the commercial variety or special-purpose periodic evaluation and rehabilitation games. Portable device 12 can include local database 15. Local database 15 stores data generated during the exercises or from vital signs monitors 27, 28, sensor 29 or external sensors 38. Portable device 12 can include removable memory card 17. Removable memory card 17 can be used to store data received from videogame 14, baseline software 19, or vital signs from vital sign monitors 27, 28, sensor 29 or external sensor 38 described below, as shown in FIG. 2.

Referring to FIG. 1, baseline software 19 runs on portable device 12. Baseline software 19 measures the capabilities of the patient using the hand held device on that particular day. The baseline is used to fine-tune parameters of videogame 14 and provide mapping between real movement and that of the patient's avatar in the game. An avatar is understood to be a bowling ball, a dart, a tennis racket, a rolling ball, or other objects that respond-to and are controlled-by the patient's movements.

As a patient exercises, an on-board memory of portable device 12 stores periodic evaluation and exercise data 21 in real time and in clinical database 20. Example variables stored are game exercise duration, maximum wrist and/or arm extension, velocity of movement scores, errors, total exercise time, and other such parameters. Periodically, a regular application uploads the files on portable device 12 to clinical database 20 on remote clinical server 22. It is preferable that exercise data 21 is uploaded at night when patient 13 is not exercising. For example, exercise data 21 can be uploaded from portable device 12 using a cell phone wireless communication means. A special authentication code can be used to identify patient 13 and store exercise data 21 correctly into remote clinical server 22.

Clinician/doctor/therapist 23 has password-protected access to remote clinical server 22. Clinician/doctor/therapist 23 prescribes the type and order of game exercises and follows patient progress. If needed, clinician/doctor/therapist 23 prescribes changes in the therapy and/or contacts patient 13 directly if exercises are not done by patient 13.

Remote clinical server 22 includes exercise scheduler and difficulty setting software 24, which can preset therapy sessions using portable device 12. Alternatively, portions of therapy sessions can reside in portable device 12. Exercise scheduler and difficulty setting software 24 prompts patient 13 to exercise at preset times and changes the difficulty as the patient progresses, or prompts patient 13 to execute a remote evaluation procedure.

Watch dog software 26 running on portable device 12 monitors the exercises performed by patient 13 to ensure that safety of patient 13 is maintained. If patient 13 exercises too long or outside prescribed motion parameters, watch dog software 26 alerts safety software 25 running in remote clinical server 22. Clinician/doctor/therapist 23 can be alerted by safety software 25 on remote clinical server 22, when exercise data 21 was not received from patient 13 as prescribed, or when a safety event was detected by portable device 12, or when a scheduled length of exercise falls below a preselected threshold.

FIG. 2 illustrates an embodiment of periodic evaluation and telerehabilitation system 10 integrated with vital sign monitoring devices. For increased safety, patient 13 can wear vital sign monitors 27 and 28. In this embodiment, periodic evaluation and telerehabilitation system 10 is capable of creating an environment in which patient 13 can play videogame 14 on portable device 12. While patient 13 exercises using videogame 14, his/her vital signs are monitored by vital sign monitors 27 and 28. Vital sign monitors 27 and 28 can be, for example, a heart rate monitor or a blood pressure monitor. It will be appreciated that additional monitors for vital signs can be used in accordance with the teachings of the present invention. Other devices or measurements can be used with portable device 12. For example, portable device 12 can include sensor 29 to measure body temperature. While playing videogame 14, patient 13 wears vital sign monitor 27 and monitor 28. Preferably, these devices are capable of transmitting monitored information to portable device 12 via wireless Bluetooth 30, or any other wireless protocol, so not to encumber patient 13 with connecting cables. Vital sign data 31 from vital sign monitors 27, 28 and sensor 29 can be stored in removable memory card 17 plugged into portable device 12.

In this embodiment, watchdog software 26 coordinates and analyzes, such as by time wise synchronization, vital sign data 31 from vital sign monitors 27 and 28 and sensor 29 with exercise data 21 from videogame 14 being played on portable device 12 and from embedded camera 60, accelerometer/goniometer 64 and other such sensors which can be an integral part of portable device 12. If a vital sign exceeds a threshold data set by clinician/doctor/therapist 23, watchdog software 26 can interrupt the rehabilitation session and notify clinician/doctor/therapist 23. Exercise data 21 and vital sign data 31 can be displayed on clinician/doctor/therapist 23 computer 32, or by other means.

Wireless router 33 can be used to provide Internet (802.11a/b/g/n) connection 34 to database server 38 on remote clinical server 22. After patient 13 has completed a rehabilitation session, application 37 on portable device 12 can transmit exercise data 21 and vital sign data 31 to remote clinical server 22 over Internet connection 34. For example, application 37 can use either 802.11b/g communication protocol or a data connection enabled by a cell phone service provider. Transmission of exercise data 21 and vital sign data 31 can be done at a scheduled time each day or immediately following each rehabilitation session. Once exercise data 21 and vital sign data 31 are received by remote clinical server 22, exercise data 21 and vital sign data 31 can be saved to remote clinical server 22, as well as being entered into clinical database 20. Clinical database 20 allows clinician/doctor/therapist 23 to monitor both patient 13 performance in videogame 14 including exercise data 21, obtained from portable device 12 and vital sign data 31 obtained from vital sign monitors 27 and 28.

The sensors not only allow for remote monitoring and evaluation, but they also allow videogame 14 to respond accordingly to the actions of patient 13. For instance, if the measurement of blood pressure from vital sign monitor 27 taken at the beginning of the exercise is outside an acceptable range, patient 13 will not be allowed to access videogame 14 and clinician/doctor/therapist 23 will be notified through watchdog software 26 and Internet connection 34.

In an example application, a ball is moved on screen 11 of portable device 12 by tilting a wrist of patient 13. Tilt sensor data from portable device 12 is measured and is stored as exercise data 21. Internet connection 34 can send exercise data 21 immediately to remote clinical server 22 to produce pseudo-real-time monitoring of game play of patient 13 with exercise scheduler and difficulty setting software 24.

Figure 3:
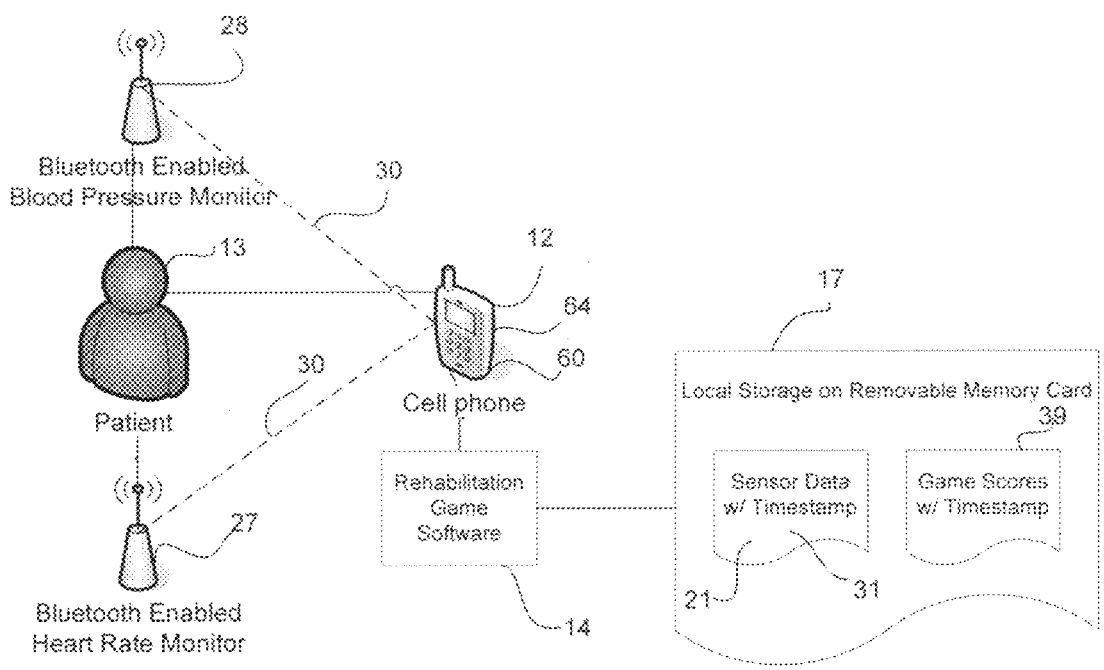
FIG. 3 is a schematic diagram of data storage during game play.

FIG. 3 is a schematic diagram of data storage during play. Exercise data 21 stored while videogame 14 is being played can comprise tilt sensor data from portable device 12 and accelerometer data from accelerometer 64. Vital sign data 31 can comprise heart rate data from vital sign monitor 27, blood pressure data from vital sign monitor 28 and skin temperature data from sensor 29. Vital sign data 31 can be data measured at the start of exercise and at the end of exercise. Some videogames 14 can use built in camera 35 to obtain data pertinent to limb position and/or orientation. Game scores 39 are associated with videogame 14 and can be relevant to show how well patient 13 performs at the task attempted. Sets of exercise data 21, vital sign data 31 and game scores 39 can be saved with timestamp applied to allow data and game scores 39 to be organized sequentially, creating a patient evaluation and recovery history.

Figure 4:
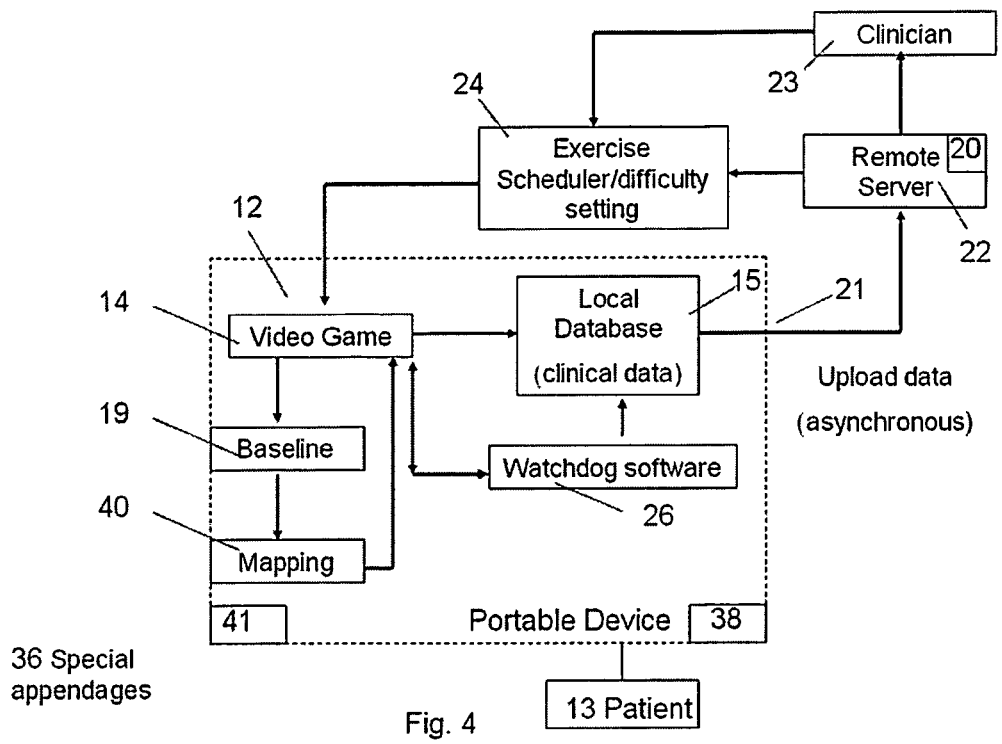
FIG. 4 is a schematic diagram of an embodiment of periodic evaluation and telerehabilitation system including videogame adaptation for rehabilitation.

FIG. 4 illustrates an embodiment of periodic evaluation and telerehabilitation system 10 including videogame adaptations for rehabilitation. This embodiment includes videogame 14, baseline software 19 and mapping software block 40 to the virtual world shown in an exercise of videogame 14. Baseline software 19 asks patient 13 to perform certain movements. During the movements, portable device 12 stores internal sensor data in local database 15. As an example such motions would be the rotation of the wrist, or that of the forearm to an extent possible in that day. Data from baseline software 19 are used by mapping software block 40 to adjust the amplification of internal sensors 41 or external sensors 38 of portable device 12 to the actions in videogame 14. This amplification makes it possible for patient 13 who is disabled to play videogame 14 on portable device 12, which otherwise would be impossible or difficult to do. It is appreciated that this amplification can lead to "electronic noise" which can be filtered with conventional methods as one taught in the art. Exercise scheduler and difficulty setting software 24 analyzes data from remote clinical server 22, to determine the number of videogames 14 and factors for mapping software block 40 to be used for a specific patient 13 in a given day.

Figure 5:
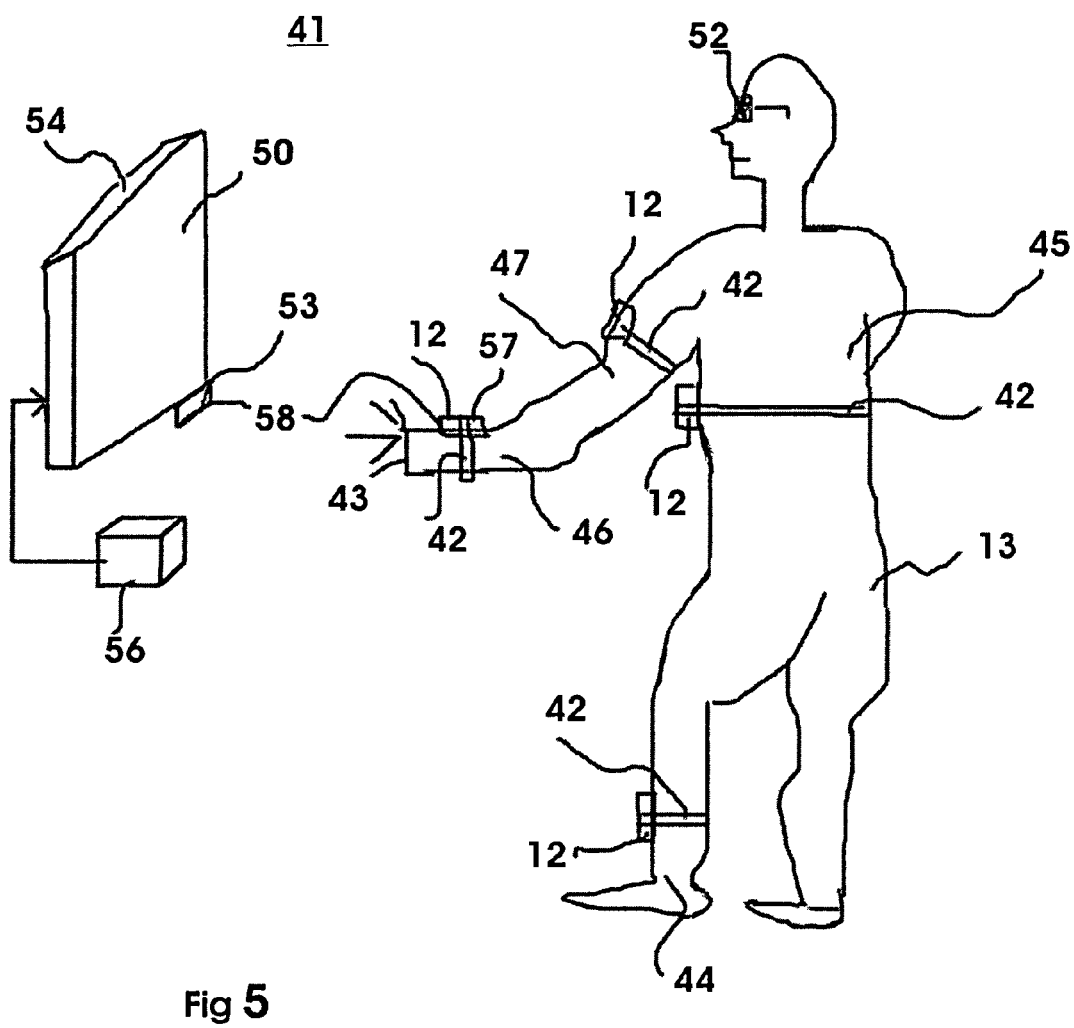
FIG. 5 is a schematic diagram of an alternate embodiment of the periodic evaluation and telerehabilitation system for rehabilitation of one or more of the wrist, forearms, torso and legs.

An embodiment of periodic evaluation and telerehabilitation system 41 for rehabilitation of one or more wrist, forearms, torso and legs is shown in FIG. 5. Coupling device 42 can be used during exercises to attach portable device 12 to an appendage. For example, coupling device 42 can be used to attach portable device 12 to hand 43. Alternatively, coupling device 42 can be used to attach portable device 12 to other body locations of patient 13, such as, for example, at ankle 44, torso 45, forearm 46, or upper arm 47 depending on which part of the body needs exercising. Typically, coupling device 42 can be a strap formed of light materials such as plastic and VELCRO®. If patients 13 are disabled, they can have difficulty holding on to portable device 12. Accordingly, periodic evaluation and telerehabilitation system 41 can be desirable for this application.

There will be situations when using only screen 11 of portable device 12 for visual feedback of patient game interaction will not suffice. This can be the case when ankle 44, torso 45, forearm 46, or upper arm 47 are exercised, and direct view of screen 11 of portable device 12 is occluded. In this embodiment, a video display 50 can be used. For example, video display 50 can be a television monitor or other video display device which is substantially larger than screen 11.

Video display device 50 can be a stereoscopic 3D television to provide improved rehabilitation results for tasks where depth perception is useful. In this embodiment, patient 13 can wear stereo glasses 52 to allow stereo viewing of TV images on video display 50. Video display 50 can control stereo glasses 52 through a control box 53, as known in the art, connected to video display 50. Video display 50 can be associated with stereo signal 54. Videogames 14 can include stereoscopic graphics. Communication between portable device 12 and video display 50 or stereo signal 54 is mediated by a wireless receiver/decoder 56 connected to video display 50 and/or stereo signal 54. Receiver/decoder 56 receives data from portable device 12 essentially duplicating that sent to screen 11 of portable device 12 and outputs digital data to video display 50 and/or stereo signal 54. It is preferred that such transmission be done over a short range, such as inside the house, such that patient 13 faces video display 50 and/or stereo signal 54. Alternatively, modem/digital port 57 of portable device 12 can be used to transmit data to video display 50 over connection 58, provided connection 58 to modem/digital port 57 does not interfere with exercises of patient 13. In one embodiment, display 50 can present stereo signal 54 viewable without glasses 52 through auto-stereoscopy, in accordance with known teachings.

Figure 6:
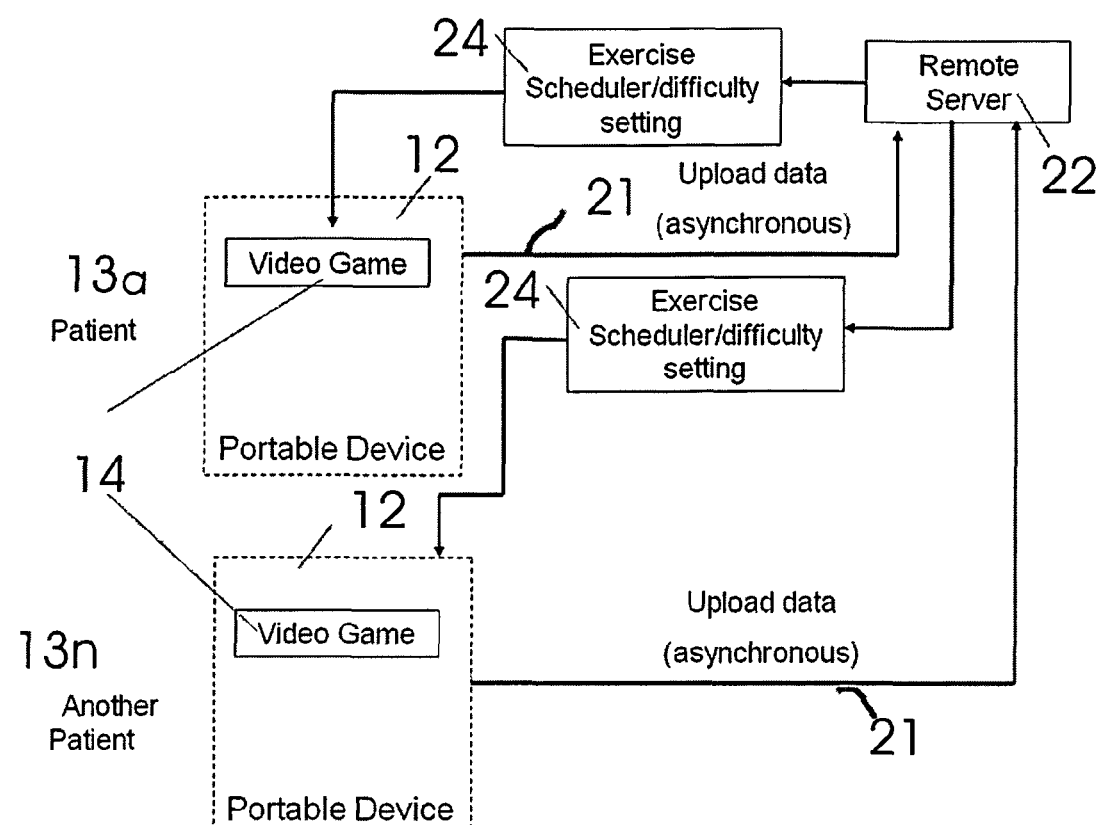
FIG. 6 is a schematic diagram of an embodiment of the periodic evaluation and telerehabilitation system for multiple users (multiplexed telerehabilitation).

Periodic evaluation and telerehabilitation system 10 can be used by a plurality of patients exercising simultaneously, as shown in FIG. 6. Patients 13a-13n can be connected simultaneously with the remote clinical server 22. Patients 13a-13n can exercise independently. Alternatively, patient 13a can play a game against patient 13n. In another scenario, teams of patients 13 can play against other teams, all their interactions being mediated by remote clinical server 22. In one embodiment, a plurality of remote clinical servers 22 can be used.

Figure 7:
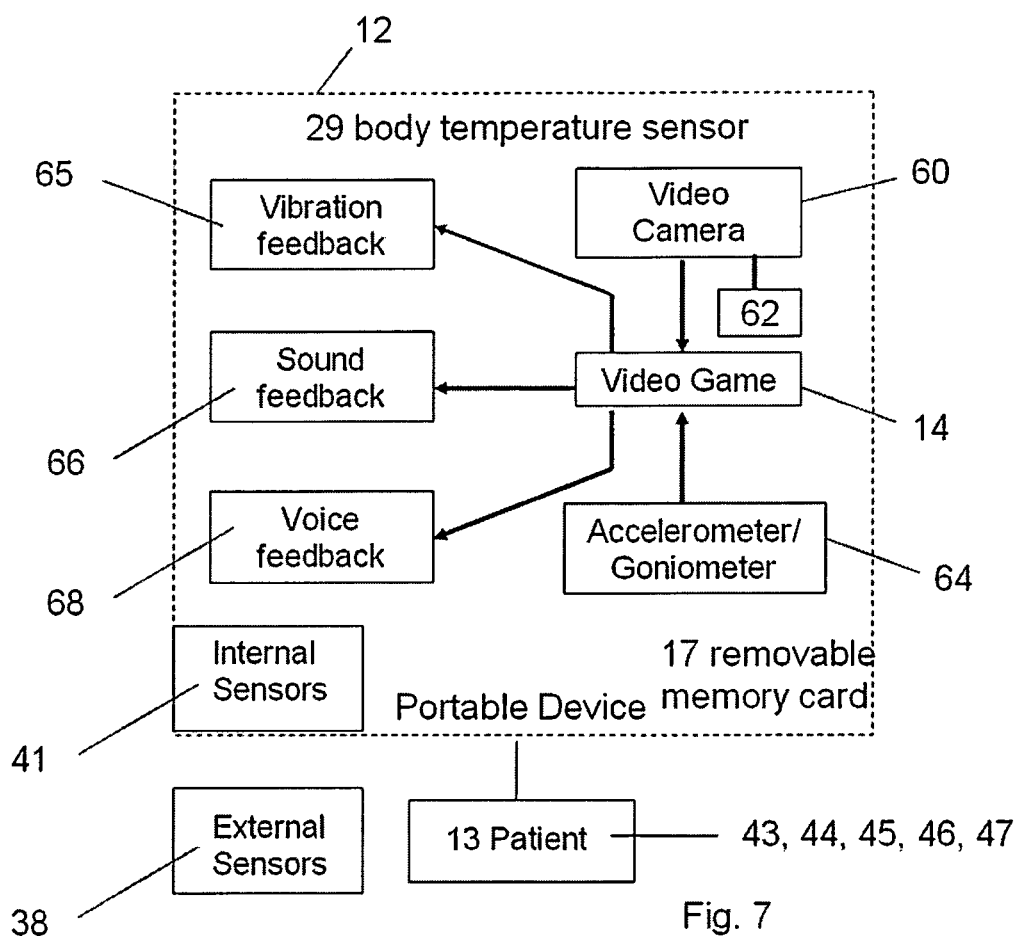
FIG. 7 is a schematic diagram of an embodiment of the portable device.

FIG. 7 illustrates an embodiment of portable device 12. Portable device 12 includes video camera 60. Video camera 60 should have sufficient resolution and processing capability to sample and process a large number of images/second. Preferably, 30 images should be sampled/processed every second. Image interpretation software 62 can be used to determine wrist and/or arm movement of patient 13 based on video data. An example of image interpretation software is manufactured by GestureTek, Canada. Alternatively, such movement can be determined by sampling portable device 12 accelerometers and goniometers assembly 64. In another embodiment, data from video camera 60 and accelerometers and goniometers assembly 64 can be combined for improved accuracy/resolution. Videogame 14 running on portable device 12 can provide multi-modal feedback to patient 13 in real time. Feedback can be in the form of vibrations or buzzing produced by vibration feedback device 65. For example, vibration feedback device 65 can be a buzzer, as used in cell phones. Another form of feedback can be sounds generated by sound feedback device 66. Sound feedback device 66 can include a speaker. Example sounds can be those generated in videogame 14, or applause or other congratulatory feedback to patient 13 to increase his/her motivation. Another form of feedback can be generated by voice feedback device 68. Voice feedback device 68 can be a voice synthesizer. Voice feedback device 68 can generate therapist artificial voice/messages to guide or motivate patient 13 in a therapy progression, following or responding to actions of patient 13. Alternatively, clinician/doctor/therapist 23 can communicate in real time with the patient 13 during an exercise if patient 13 has difficulty and requests assistance, or if patient 13 needs more guidance when performing a periodic evaluation procedure.

Portable device 12 has different videogames 14 originally designed for entertainment. It is known in the art that such videogames 14 can be designed using Symbian C++, Python, and Java programming languages. Videogame 14 can be adapted for periodic evaluation and rehabilitation applications. Videogames 14 can be developed specifically for rehabilitation of an area, encouraging repeated movements of one or more affected appendages, such as hand 43, ankle 44, torso 45, forearm 46, or upper arm 47.

Figure 8:
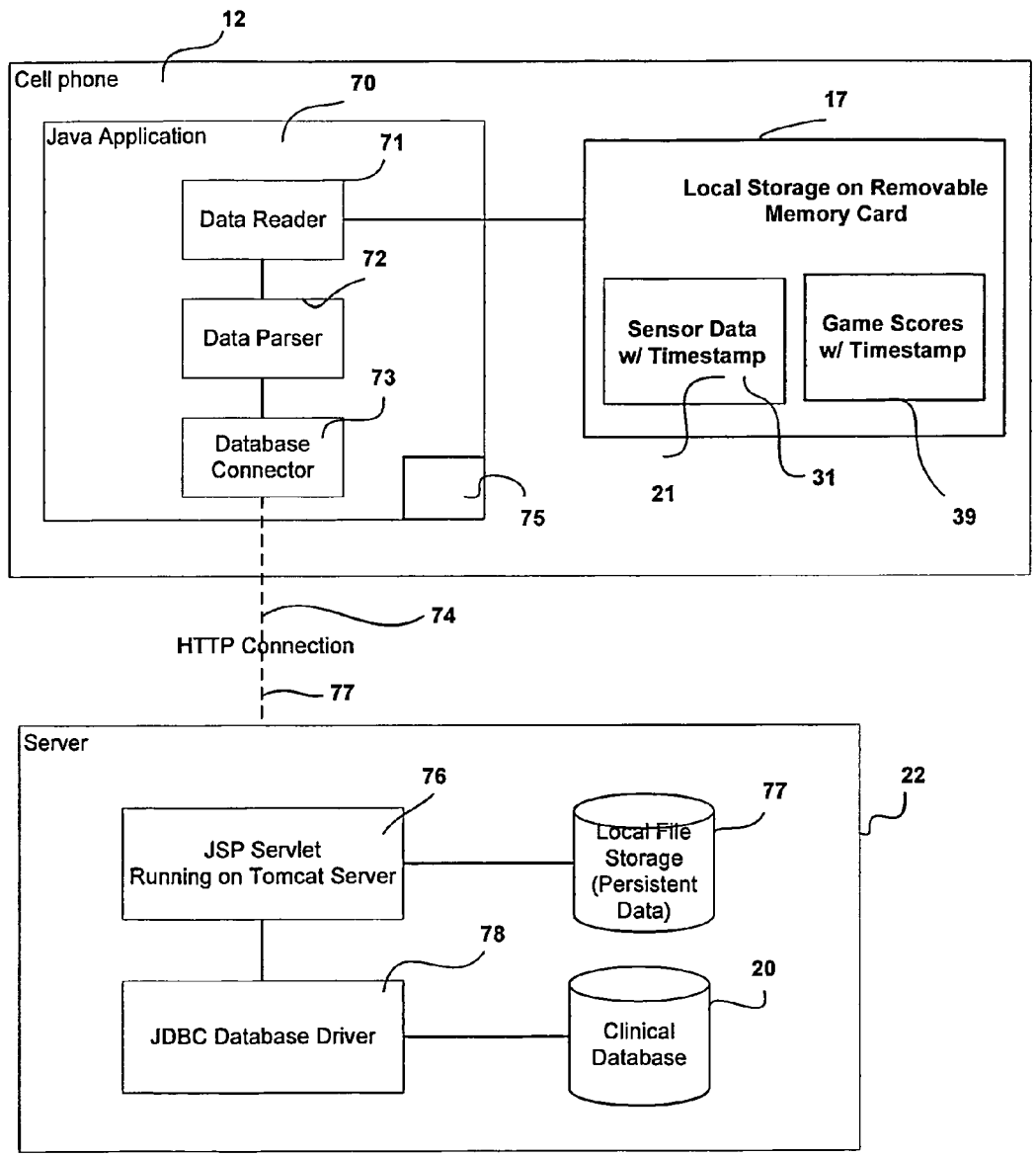
FIG. 8 is a schematic diagram of data storage of the portable device and uploading to a remote clinical server.

When played, videogame 14 stores the exercise data into a file stored in a sent folder on removable memory card 17, as shown in FIG. 8. For example, removable memory card 17 can be an external MSD (Micro Secure Data) card. Typically, removable memory cards have a capacity of up to 16 GB. After storage of data into a folder in removable memory card 17, application 70 running in the background on portable device 12 reads data from removable memory card 17 using data reader 71. Data are parsed with data parser 72. Application 70 initiates an HTTP connection request 73 to remote clinical server 22. For example, application 70 can be designed in Java ME. As soon as HTTP connection request 73 is accepted, HTTP connection 74 is established and application program 70 sends files including data to remote clinical server 22. Typically, one file can be sent with each HTTP connection request 73. If the file was sent successfully, it moves to archive folder 75 for storage on portable device 12, otherwise the file remains in the sent folder to be sent later. Remote clinical server 22 can include JSP servlet 76 running continuously with clinical database 20 on remote clinical server 22. For example, JSP servlet can run on a Tomcat server. JSP servlet 76 receives connection requests from the portable device 12. JSP servlet 76 then parses the request, and stores the data sent from portable device 12 into local storage file 77. Remote clinical server 22 can receive multiple connections at the same time from multiple portable devices 12 used by patients 13a-13n as in multiplexed rehabilitation settings described above. It is appreciated, however, that periodic evaluations will not be multiplexed, rather done one-to-one between the remote clinician/doctor/therapist 23 and patient 13. Once the files are stored on JSP servlet 76 they are parsed and entered into clinical database 20, such as by using another Java application JSP servlet 76. The division of the receiving and parsing of the file into two separate tasks is done to allow storing the files despite the connection between JSP servlet 76 and clinical database 20. Accordingly, if the connection between clinical database 20 and database driver 78 of remote clinical server 22 is broken, the files are still safely stored. Once files are parsed correctly and stored in clinical database 20 they are moved into a storage archive.

The periodic evaluation and telerehabilitation system of the present invention provides live monitoring of the patient's heart rate from vital sign monitor 27 and blood pressure from vital sign monitor 28. These values can be transferred to remote clinical server 22 while patient 13 is playing videogame 14 or is being evaluated. Using the same protocol of forwarding HTTP connection request 73 to JSP servlet 76, periodic evaluation and telerehabilitation system 10 can monitor the heart rate, blood pressure or skin temperature of patient 13 and can stop patient 13 from playing videogame 14 if the values exceed the safety threshold previously set by clinician/doctor/therapist 23, and can notify clinician/doctor/therapist 23 immediately to follow up with patient 13.

Figure 9:
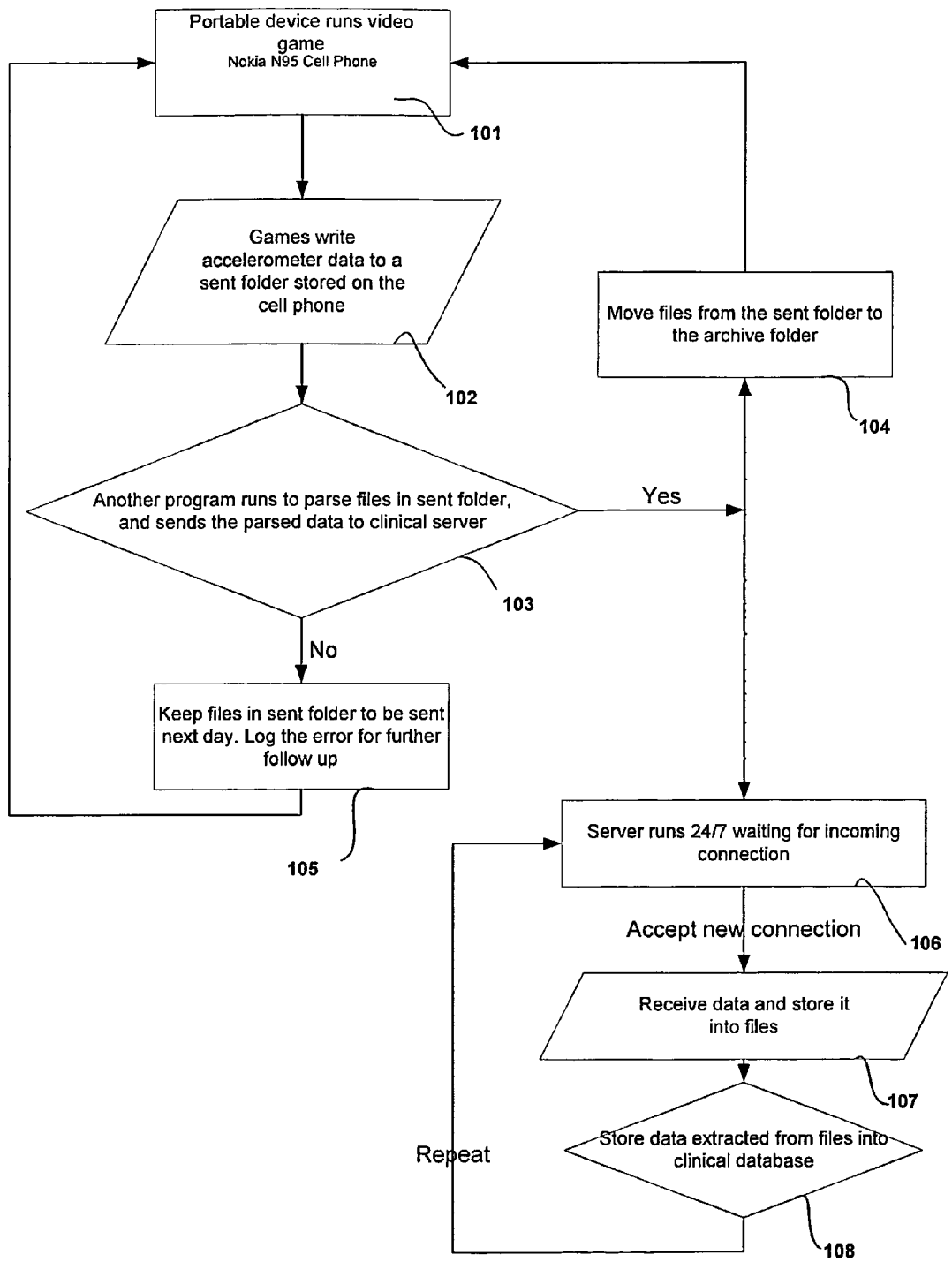
FIG. 9 is a flow diagram of data retrieval from the portable device to the remote clinical server.

FIG. 9 is a flow chart for data retrieval process between portable device 12 and remote clinical server 22. In block 101, data is received at the portable device from playing with videogame 14 and/or from video camera 60 or accelerometers and goniometers assembly 64. In block 102, data are written to a sent folder stored in the portable device. In block 103, an application program parses files in the sent file and sends the data to the remote clinical server. If the data is sent from block 103, files are moved from the sent folder to an archive folder in block 104. If the data is not sent from block 103, files are kept in the sent folder in block 105. Block 105 can also log the error for follow up and for sending the files at a subsequent time.

In block 106, the remote clinical server is continuously waiting for an incoming connection. If a new connection is established, data from portable device 12 are received and stored into files at the remote clinical server in block 107. In block 108, data extracted from the files are stored into a database. Blocks 106 through 108 are repeated.

FIG. 10 is an illustration of the use of a web portal for data retrieval in periodic evaluation and telerehabilitation system 10. Clinician/doctor/therapist 23, using a password-protected web portal 200 on remote clinical server 22, can access different patients 13a-13n and their profiles, review their progress and their training session history and interactively change their next rehabilitation session. Web portal 200 can also be accessed by patient computer 202. Patient(s) 13 using patient computer 202 can access their own charts in order to see their progress. Graphs can be generated automatically to facilitate comprehension of the data at web portal 200. Clinical database 20 can also automatically monitor the sessions and report to clinician/doctor/therapist 23 if patient(s) 13 are missing their exercises, doing them incorrectly or spending more than the allowed amount of time for the exercises. Web portal 200 can include authorization module 204 for providing authorization to data stored in remote clinical database 20. Web portal 200 provides security for such private data of clinical database 20. Web portal 200 also provides remote access to the data stored on clinical database 20 through Internet connection 34.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A system for periodic evaluation and telerehabilitation of a disabled user having a body part, comprising:
  a portable processing device; said portable device adapted to be held or attached to said body part of said disabled user;
  an animated or virtual reality sequence forming a videogame, said videogame being processed on said portable device to provide directions to said disabled user so as to elicit movements of said body part by said disabled user;
  means for capturing exercise data resulting from interaction of said user with said videogame;
  means for measuring a baseline of said disabled user based on a subset of the directions to said disabled user that direct said disabled user to move parts of said disabled user's body;
  means for mapping said measured baseline with said videogame for tuning said videogame by adjusting amplification of said means for capturing exercise data to provide mapping between real movement of said disabled user and movement of said avatar during said videogame so that movement of the avatar appears greater than the real movement of said disabled user;
  remote clinical server means for receiving said exercise data; and storing means for storing said exercise data at said remote clinical server, the exercise data including errors and game duration;
exercise scheduler and difficulty setting means for setting a therapy session using said portable device in accordance with said exercise data including errors and game duration, wherein said therapy session controls a length and a difficulty of said videogame being processed on said portable processing device in accordance with said exercise data including errors and game duration.

2. The system of claim 1 wherein a clinician/doctor/therapist can access said therapy session on a web portal to follow a history of a therapy session of said user.

3. The system of claim 1 wherein a clinician/doctor/therapist can access said therapy session and coach a remote said user in real time.

4. The system of claim 1 further comprising:
one or more vital sign monitors, said vital sign monitors capturing vital sign data for a vital sign of said disabled user and said remote clinical server means receiving said vital sign data.

5. The system of claim 4 further comprising means for synchronizing said exercise data with said vital sign data at said remote clinical server.

6. The system of claim 5 wherein said portable device includes a sensor to measure body temperature data and said remote clinical server means receiving said body temperature data.

7. The system of claim 6 further comprising watchdog means, said watchdog means interrupting said therapy session if said vital sign data and/or said body temperature data, and/or duration of play of said videogame in said therapy session exceeds a threshold and further comprising means for notifying an authorizer of said therapy session.

8. The system of claim 4 wherein said portable device includes a removable memory card for storing said exercise data and/or said vital sign data.

9. The system of claim 4 further comprising a web portal at said remote clinical server means, said web portal adapted to access said exercise data and said vital sign data.

10. The system of claim 1 further comprising:
watchdog means for monitoring said movements of said disabled user, said watchdog means ensuring that safety of said disabled user is maintained; and
safety means at said remote clinical server, said safety means alerting a clinician or doctor or therapist accessing said remote clinical server when data was not received from said disabled user as prescribed, or when a safety event was detected by said portable device or when a scheduled length of exercise by said interaction of said disabled user with said videogame falls below a preselected threshold.

11. The system of claim 1 wherein said portable device comprises a cell phone.

12. The system of claim 1 further comprising:
means for displaying said videogame to said user.

13. The system of claim 12 wherein said means for displaying said videogame to said user is a video display.

14. The system of claim 12 wherein said means for displaying said videogame to said user is a stereoscopic 3D television and said videogame includes a stereoscopic videogame.

15. The system of claim 14 further comprising stereo glasses adapted to be worn by said disabled user.

16. The system of claim 1 wherein said means for capturing exercise data comprises:
an accelerator and/or goniometer.

17. The system of claim 1 wherein said means for capturing exercise data comprises:
a video camera and means for interpreting video data from said video camera.

18. The system of claim 1 wherein said means for capturing exercise data comprises:
an accelerator and/or goniometer in combination with a video camera and means for interpreting video data from said video camera.

19. The system of claim 1 wherein said portable device is held in a hand of said disabled user.

20. The system of claim 1 wherein said storing means is a database.

21. The system of claim 1 wherein said exercise data includes one or more of game exercise duration, maximum wrist and/or arm extension, velocity of movement, score of videogame, errors, and total exercise time.

22. The system of claim 1 further comprising a plurality of said portable devices, said remote clinical server means receiving said exercise data from said plurality of portable devices wherein said system provides multiplexed rehabilitation to rehabilitate said plurality of users each connected to said remote clinical server means.

23. The system of claim 22 wherein said plurality of disabled users can play independently or against one another during said telerehabilitation.

24. The system of claim 1 wherein said videogame is a sequence of videogames.

25. A method for telerehabilitation comprising the steps of:
holding or coupling a portable computing device to a body part of a disabled user;
executing on said portable computing device an animated or virtual reality sequence forming a videogame to provide directions to the disabled user;
capturing exercise data resulting from movement of said body part upon interaction of said disabled user with said videogame, said exercise data including errors and game duration;
the portable computing device causing an avatar to be displayed, wherein movement of the avatar is related to movement of said body part;
measuring a baseline of the disabled user based on a subset of the directions to the disabled user that direct the disabled user to move parts of the disabled user's arm;
mapping the measured baseline with the videogame for tuning the videogame by adjusting amplification of captured exercise data to provide mapping between real movement of said disabled user and movement of said avatar during said videogame so that movement of the avatar appears greater than the real movement of said disabled user;
receiving said exercise data at a remote clinical server;
storing said exercise data at said remote clinical server; and
a processor determining a therapy session using said portable computing device by controlling the length, type, and difficulty of said videogame being executed on said portable computing device in accordance with said exercise data including errors and game duration.

26. The method of claim 25 further comprising the steps of:
capturing vital sign data for a vital sign of said disabled user and receiving said vital sign data at said remote clinical server.

27. The method of claim 26 further comprising the step of:
synchronizing said exercise data with said vital sign data at said remote clinical server.

* * * * *